(12) United States Patent
Ohta et al.

(10) Patent No.: US 11,124,657 B2
(45) Date of Patent: Sep. 21, 2021

(54) TRANSPARENT LAMINATE

(71) Applicant: Dexerials Corporation, Tokyo (JP)

(72) Inventors: Eiji Ohta, Tokyo (JP); Masayasu Kakinuma, Tokyo (JP); Masaki Takenouchi, Tokyo (JP); Satoshi Kawamura, Tokyo (JP); Kiyoaki Tanifuji, Tokyo (JP); Emi Yoshida, Tokyo (JP); Kimitaka Nishimura, Tokyo (JP); Shunichi Kajiya, Tokyo (JP); Shigehisa Ohkawara, Tokyo (JP); Maki Ogawa, Tokyo (JP)

(73) Assignee: Dexerials Corporation, Tokyo (JP)

( * ) Notice: Subject to any disclaimer, the term of this patent is extended or adjusted under 35 U.S.C. 154(b) by 359 days.

(21) Appl. No.: 15/574,619

(22) PCT Filed: May 13, 2016

(86) PCT No.: PCT/JP2016/064225
§ 371 (c)(1),
(2) Date: Nov. 16, 2017

(87) PCT Pub. No.: WO2016/186013
PCT Pub. Date: Nov. 24, 2016

(65) Prior Publication Data
US 2018/0148578 A1     May 31, 2018

(30) Foreign Application Priority Data
May 9, 2016     (JP) .............................. JP2016-094023

(51) Int. Cl.
*C09D 5/00*     (2006.01)
*G02B 1/118*     (2015.01)
(Continued)

(52) U.S. Cl.
CPC ............ *C09D 5/00* (2013.01); *A41D 13/1184* (2013.01); *A61F 9/02* (2013.01); *A61F 9/029* (2013.01);
(Continued)

(58) Field of Classification Search
CPC ...... C09D 5/00; C09D 135/02; C09D 133/24; C08F 220/34; C08F 222/1006;
(Continued)

(56) References Cited

U.S. PATENT DOCUMENTS

2007/0242357 A1   10/2007 Thakkar et al.
2010/0323165 A1   12/2010 Sakuma et al.
(Continued)

FOREIGN PATENT DOCUMENTS

JP     2006-152105     6/2006
JP     2009-271298     11/2009
(Continued)

*Primary Examiner* — Nancy R Johnson
(74) *Attorney, Agent, or Firm* — Carmody Torrance Sandak & Hennessey LLP

(57) ABSTRACT

A transparent laminate including a transparent substrate and structure layer, wherein the structure layer contains protrusion portions, depression portions, or both on a surface thereof, and an average distance between the adjacent protrusion portions or between the adjacent depression portions is equal to or less than a visible light wavelength, the structure layer includes a polymerized product of an active energy ray curable resin composition, the resin composition includes a composition of a (meth)acryloyl group-containing polymerizable compound, the compound composition includes one or more from each of (A), (B), and (C):
(A) a monofunctional (meth)acryloyl group-containing polymerizable compound;
(B) alkylene glycol di(meth)acrylate; and
(C) trifunctional or higher (meth)acrylate,
(Continued)

the (A) satisfies certain conditions specifying a type and amount of a compound, and a ratio ($E'_{150}/E'_{50}$) of storage elastic modulus $E'_{150}$ of the structure layer at 150° C. to storage elastic modulus $E'_{50}$ thereof at 50° C. is 0.5 or less.

8 Claims, 8 Drawing Sheets

(51) Int. Cl.
| | | |
|---|---|---|
| *G02B 1/111* | (2015.01) | |
| *A61F 9/02* | (2006.01) | |
| *C08F 220/34* | (2006.01) | |
| *G02B 1/18* | (2015.01) | |
| *A41D 13/11* | (2006.01) | |
| *C08F 220/58* | (2006.01) | |
| *C08F 222/10* | (2006.01) | |
| *C08J 3/28* | (2006.01) | |
| *C09D 133/24* | (2006.01) | |
| *C09D 135/02* | (2006.01) | |

(52) U.S. Cl.
CPC .......... *C08F 220/34* (2013.01); *C08F 220/58* (2013.01); *C08F 222/1006* (2013.01); *C08J 3/28* (2013.01); *C09D 133/24* (2013.01); *C09D 135/02* (2013.01); *G02B 1/111* (2013.01); *G02B 1/118* (2013.01); *G02B 1/18* (2015.01); *C08J 2333/24* (2013.01); *C08J 2335/02* (2013.01)

(58) Field of Classification Search
CPC .......... C08F 220/58; A61F 9/02; A61F 9/029; G02B 1/111; G02B 1/18; G02B 1/118; C08J 3/28; C08J 2335/02; C08J 2333/24; A41D 13/1184; B32B 2307/51; B32B 2307/412; B32B 27/16; B32B 27/308
See application file for complete search history.

(56) References Cited

U.S. PATENT DOCUMENTS

| | | | |
|---|---|---|---|
| 2013/0004718 A1 | 1/2013 | Takihara et al. | |
| 2014/0098422 A1* | 4/2014 | Fukuda | B29D 11/00346 |
| | | | 359/601 |
| 2014/0127463 A1 | 5/2014 | Otani et al. | |
| 2016/0052227 A1 | 2/2016 | Takihara et al. | |

FOREIGN PATENT DOCUMENTS

| | | |
|---|---|---|
| JP | 2010-091689 | 4/2010 |
| JP | 4689718 | 5/2011 |
| WO | 2011/115162 | 9/2011 |
| WO | 2013/005769 | 1/2013 |

\* cited by examiner

TRANSPARENT LAMINATE

TECHNICAL FIELD

The present invention relates to a transparent laminate.

BACKGROUND ART

Shields or goggles formed of transparent plastics have been conventionally used for the purpose of reducing pollutions against faces or eyes caused by splashes of coating or process powder during industrial precision operations, or for the purpose of protecting from sputtered substances.

Moreover, eye shields or face shields formed of transparent plastics are used for medical applications for the purpose of preventing infections from splashes during treatments performed to patients, or for the purpose of protecting a face from sputtered substances during surgical operations.

Furthermore, proposed is a shield formed of a transparent substrate that corresponds to a current diagnostic imaging device having a 3D display function and does not impair polarization optical properties for a 3D display.

Several products are commercially available as a shield for protecting eyes. However, shields having excellent visibility with low reflection and desired transparency are desired because reductions in work efficiency or fatigue of users may be caused by reductions in visibility when a transmittance is reduced due to surface reflection of the shield or external light reflection is caused.

Moreover, shields having excellent anti-fogging are desired because visibility is impaired when the shields are fogged by breath of users wearing the shields.

Meanwhile, when splashes of powder or pollutants from which users are to be protected are deposited on a shield, it is preferred that the shield be continuously used after wiping the splashed deposit out with cotton or non-woven fabric, if the deposit is a slight degree of splashes. In the case where a shield has a surface having excellent hydrophobicity in order to obtain anti-fogging, there is a problem that a wiping capability may be impaired because the surface has excellent compatibility to aqueous pollutants. Accordingly, shields excel in both anti-fogging and a wiping capability considering a balance of both properties are desired.

In order to suppress influences to display visibility of a 3D display, moreover, shields having excellent visibility that do not impair polarization properties of 3D displays are desired.

In the case where the shield is formed by laminating, on a substrate, a cured product layer formed of a cured product of an active energy ray curable resin (may be referred to as a resin composition hereinafter) and having a fine protrusion and depression structure, moreover, the shield is desired to be a shield excels in both adhesion and releasability, where adhesion between the substrate and the cured product layer is excellent and releasability between a master used in a production of the cured product layer and the cured product layer.

Proposed is a transparent laminate that is a transparent laminate in which a cured product layer formed of a cured product of an active energy ray curable resin composition and having a fine protrusion and depression structure is laminated on a substrate, and is a transparent laminate to which antifouling or abrasion resistance has been provided (see, for example, PTL 1).

Moreover, proposed is a transparent laminate that is a transparent laminate in which a cured product layer formed of a cured product of an active energy ray curable resin composition and having a fine protrusion and depression structure is laminated on a substrate, and is a transparent laminate to which lubricity, abrasion resistance, or fingerprint wiping capability has been provided (see, for example, PTL 2).

Furthermore, proposed is a transparent laminate that is a transparent laminate in which triacetyl cellulose (TAC) is used for a substrate in view of optical transparency or birefringence, and a cured product layer formed of a cured product of an active energy ray curable resin composition and having a fine protrusion and depression structure is laminated on the substrate, and is a transparent laminate to which adhesion is provided (see, for example, PTL 3).

CITATION LIST

Patent Literatures

PTL 1: Japanese Patent No. 4689718
PTL 2: International Publication No. WO 2011/115162
PTL 3: International Publication No. WO 2013/005769

SUMMARY OF INVENTION

Technical Problem

However, the transparent laminate disclosed in PTL 1 does not have sufficiently satisfactory wiping capability against pollutants because the transparent laminate has a composition that gives a low water contact angle. Moreover, the transparent laminate disclosed in PTL 2 includes, as an essential component, a monomer having 2 radical functional groups per molecule and 11 or more oxyalkylene groups per molecule. As demonstrated in Comparative Example 4 described later, the transparent laminate including a difunctional monomer including a polyoxyalkylene group has a low water contact angle and does not have satisfactory wiping capability against pollutants.

In PTL 3, moreover, a difunctional monomer having 4 or less oxyalkylene groups per molecule is an essential structural component. As described earlier, however, a water contact angle is low and wiping capability against pollutants is not satisfactory when a difunctional monomer having a polyoxyalkylene group used in Examples of PTL 3 is included (see Comparative Example 4).

In PTL 3, furthermore, an internal lubricant is included in a resin composition in order to impart lubricity from a mold. When such a secondary material is included, adhesion to a substrate may be reduced. Therefore, there is a need for a transparent laminate that does not include such a secondary material and excels in both adhesion and releasability.

In view of realization of a transparent laminate having excellent transparency with low reflection and excellent visibility that does not impair polarization properties of 3D displays, excellent anti-fogging and wiping capability, and excellent adhesion to a substrate and releasability from a master, the transparent laminate disclosed in any of PTL 1 to PTL 3 is not sufficient and further improvements need to be made.

The present invention aims to solve the above-mentioned various problems existing in the art and to achieve the following object. Namely, the present invention has an object to provide a transparent laminate that has excellent transparency with low reflection and has excellent visibility that does not impair polarization properties of 3D displays, has excellent anti-fogging and wiping capability, and excellent adhesion to a substrate and excellent releasability from a master.

Solution to Problem

Solutions for solving the problems are as follows.
<1> A transparent laminate including:
  a transparent substrate; and
  a structure layer,
wherein the structure layer contains protrusion portions, depression portions, or both on a surface of the structure layer, and an average distance between the adjacent protrusion portions or an average distance between the adjacent depression portions is equal to or less than a wavelength of visible light,
the structure layer includes a polymerized product of an active energy ray curable resin composition,
the active energy ray curable resin composition includes a composition of a (meth)acryloyl group-containing polymerizable compound,
the composition of a (meth)acryloyl group-containing polymerizable compound includes one or more of (A) below, one or more of (B) below, and one or more of (C) below:
  (A) a monofunctional (meth)acryloyl group-containing polymerizable compound;
  (B) alkylene glycol di(meth)acrylate; and
  (C) trifunctional or higher (meth)acrylate,
the (A) monofunctional (meth)acryloyl group-containing polymerizable compound satisfies (A-1) below or (A-2) below:
  (A-1) a nitrogen-containing monofunctional (meth)acryloyl group-containing polymerizable compound that includes nitrogen in a structure thereof included but a nitrogen-free monofunctional (meth)acryloyl group-containing polymerizable compound that does not include nitrogen in a structure thereof is not included, and an amount of the nitrogen-containing monofunctional (meth)acryloyl group-containing polymerizable compound in the active energy ray curable resin composition is 20% by mass or greater; and
  (A-2) a nitrogen-containing monofunctional (meth)acryloyl group-containing polymerizable compound that includes nitrogen in a structure thereof and a nitrogen-free monofunctional (meth)acryloyl group-containing polymerizable compound that does not include nitrogen in a structure thereof are included, an amount of the nitrogen-containing monofunctional (meth)acryloyl group-containing polymerizable compound in the active energy ray curable resin composition is 20% by mass or greater, and an amount of the nitrogen-free monofunctional (meth)acryloyl group-containing polymerizable compound in the active energy ray curable resin composition is 22% by mass or less, and
a ratio ($E'_{150}/E'_{50}$) of storage elastic modulus $E'_{150}$ of the structure layer at 150° C. to storage elastic modulus $E'_{50}$ of the structure layer at 50° C. is 0.5 or less.
<2> The transparent laminate according to <1>,
wherein the nitrogen-containing monofunctional (meth)acryloyl group-containing polymerizable compound includes a cyclic structure containing nitrogen in a molecule thereof.
<3.> The transparent laminate according to <2>,
wherein the nitrogen-containing monofunctional (meth)acryloyl group-containing polymerizable compound is acryloyl morpholine.
<4> The transparent laminate according to <1>,
wherein the nitrogen-free monofunctional (meth)acryloyl group-containing polymerizable compound includes a cyclic structure containing oxygen in a molecule thereof.
<5> The transparent laminate according to <4>,
wherein the nitrogen-free monofunctional (meth)acryloyl group-containing polymerizable compound is tetrahydrofurfuryl acrylate.
<6> The transparent laminate according to <1>,
wherein the (C) trifunctional or higher (meth)acrylate is trifunctional (meth)acrylate.
<7> The transparent laminate according to <6>,
wherein the (C) trifunctional or higher (meth)acrylate is trifunctional (meth)acrylate and trifunctional or higher urethane acrylate.
<8> The transparent laminate according to any one of <1> to <7>,
wherein a water contact angle on a surface of the structure layer is 26° or greater.
<9> The transparent laminate according to any one of <1> to <8>,
wherein an in-plane retardation value of the transparent substrate is 20 nm or less.
<10> An optical element for face including:
  the transparent laminate according to any one of <1> to <9>.

Advantageous Effects of Invention

The present invention can solve the above-described various problems existing in the art, can achieve the above-mentioned object, and can provide a transparent laminate, which has excellent transparency with low reflection, has excellent visibility that does not impair polarization properties of 3D displays, has excellent anti-fogging and wiping capability, and also has excellent adhesion to a substrate and excellent releasability from a master.

DESCRIPTION OF EMBODIMENTS (Transparent Laminate)

Figure 1A:
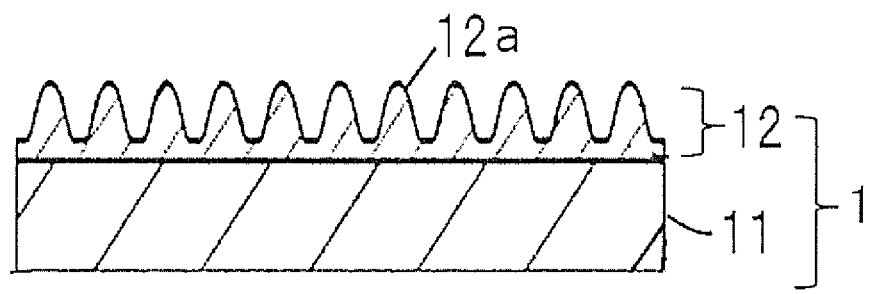
FIG. 1A is a cross-sectional view illustrating one configuration example of the transparent laminate of the present invention.

The transparent laminate of the present invention includes at least a transparent substrate and a structure layer, and further includes other members, if necessary.

The structure layer contains protrusion portions, depression portions, or both on the surface thereof, and the average distance between the adjacent protrusion portions or the average distance between the adjacent depression portions is equal to or less than a wavelength of visible light.

The structure layer includes a polymerized product of an active energy ray curable resin composition.

The active energy ray curable resin composition includes a composition of a (meth)acryloyl group-containing polymerizable compound.

The composition of a (meth)acryloyl group-containing polymerizable compound includes one or more of (A) below, one or more of (B) below, and one or more of (C) below:

(A) a monofunctional (meth)acryloyl group-containing polymerizable compound;

(B) alkylene glycol di(meth)acrylate; and (C) trifunctional or higher (meth)acrylate.

The (A) monofunctional (meth)acryloyl group-containing polymerizable compound satisfies (A-1) below or (A-2) below:

(A-1) A nitrogen-containing monofunctional (meth)acryloyl group-containing polymerizable compound that includes nitrogen in a structure thereof is included but a nitrogen-free monofunctional (meth)acryloyl group-containing polymerizable compound that does not include nitrogen in a structure thereof is not included, and an amount of the nitrogen-containing monofunctional (meth)acryloyl group-containing polymerizable compound in the active energy ray curable resin composition is 20% by mass or greater; and (A-2) A nitrogen-containing monofunctional (meth)acryloyl group-containing polymerizable compound that includes nitrogen in a structure thereof and a nitrogen-free monofunctional (meth)acryloyl group-containing polymerizable compound that does not include nitrogen in a structure thereof are included, an amount of the nitrogen-containing monofunctional (meth)acryloyl group-containing polymerizable compound in the active energy ray curable resin composition is 20% by mass or greater, and an amount of the nitrogen-free monofunctional (meth)acryloyl group-containing polymerizable compound in the active energy ray curable resin composition is 22% by mass or less.

A ratio ($E'_{150}/E'_{50}$) of storage elastic modulus $E'_{150}$ of the structure layer at 150° C. to storage elastic modulus $E'_{50}$ of the structure layer at 50° C. is 0.5 or less.

Note that, in the present invention, (meth)acrylate means acrylate or methacrylate. Moreover, a (meth)acryl-based resin means an acryl-based resin or a methacryl-based resin.

The present inventors performed researches on a composition of a material constituting a transparent laminate including a transparent substrate having a fine and dense protrusion and depression (moth-eye) structure and properties the transparent laminate exhibits. As a result, the present inventors have found that a transparent laminate that has a resin composition having the above-mentioned specific structural components, and satisfies the above-mentioned elements specifying the ratio of the storage elastic modulus of the structure layer can exhibits excellent results on all of the items listed in the above-described problem, including visibility, anti-fogging, wiping capability, adhesion, and releasability with a good balance.

In PTL 2 and PTL 3 above, for example, PTL 2 mentions as a requirement that a molecular weight per functional group is 110 to 200 in a monomer having 3 or more radical polymerizable functional groups per molecule, and PTL 3 mentions as a requirement that a molecular weight per functional group is 150 or less in the monomer having 3 or more radical polymerizable functional groups per molecule. Moreover, PTL 2 mentions as a requirement that a monomer having 2 or more radical polymerizable functional groups per molecule is a monomer having 11 or more oxyalkylene groups per molecule, and PTL 3 mentions as a requirement that the monomer having 2 or more radical polymerizable functional groups per molecule is a monomer having 4 or less oxyalkylene groups per molecule. Specifically, PTL 2 and PTL 3 above specify components of opposite requirements. As described here, constitutional components of a resin composition are completely different depending on the intended purpose or a relationship with other constitutional components.

The present inventors performed researches on a resin composition exhibiting excellent results on all of the items of visibility, anti-fogging, wiping capability, adhesion, and releasability. As a result, the present inventors have found that the specific constitutional components above are effective.

One example of a cross-sectional view of the configuration of the transparent laminate of the present invention is illustrated in FIGS. 1A and B. As illustrated in FIGS. 1A and B, this transparent laminate 1 has a fine depression and protrusion structure (hereinafter, also referred to as "moth-eye structure") whose size is equal to or less than visible wavelengths from several tens nm to several hundreds nm, on the surface thereof.

The transparent laminate 1 includes a transparent substrate 11, and a structure layer 12 having a plurality of structures 12a including protrusion portions or depression portions at an interval equal to or less than a wavelength of visible light (360 nm to 830 nm) on the surface thereof.

Figure 2:
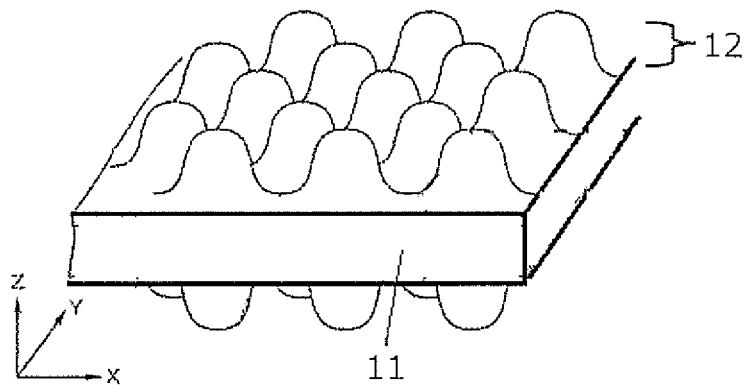
FIG. 2 is a perspective view illustrating one example of the surface shape of the transparent laminate of the present invention.

While protrusion or depression structures 12a are formed on the surface of the structure layer 12, the plurality of structures 12a are arranged so as to form a plurality of rows. FIG. 2 illustrates one example of a perspective view of the transparent laminate of the present invention, the transparent laminate including a protrusion structure layer 12 on the surface thereof.

Figure 1B:
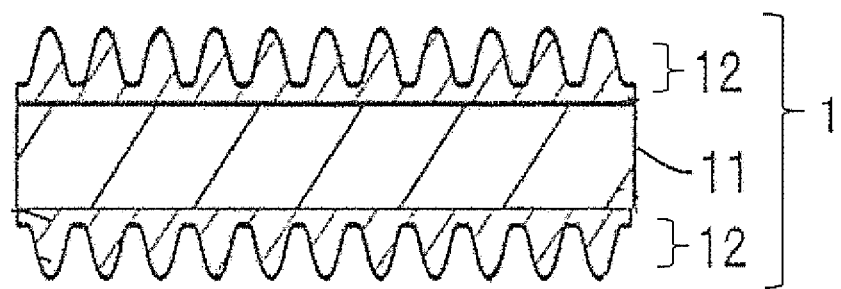
FIG. 1B is a cross-sectional view illustrating another configuration example of the transparent laminate of the present invention.

The transparent laminate of the present invention may include a structure layer 12 where fine depression and protrusion structures 12a are formed, on both front and rear surfaces of the transparent substrate 11 (FIG. 1B).

A transparent laminate including fine and dense depression and protrusion on each of both surfaces thereof can effectively suppress reflection at the interface between the transparent laminate and air. The transparent laminate can be said to be a preferable aspect because of being excellent in visibility such as permeation properties and reflection properties.

The transparent laminate 1 has, for example, transparency to visible light, and the refractive index n thereof is preferably 1.40 or more and 2.00 or less, more preferably 1.43 or more and 2.00 or less.

The refractive index of the structure layer 12 is preferably the same or almost the same as the refractive index of the transparent substrate 11. The reason for this is because internal reflection can be suppressed to result in an enhancement in contrast. With the structure of the transparent laminate illustrated in FIG. 1A or FIG. 1B, a refractive index of the transparent substrate 11 and a refractive index of the structure layer 12 may not be matched completely and may be close to each other, for example, the refractive index of the transparent substrate 11 is 1.48 to 1.50, and the refractive index of the structure layer 12 is 1.51 to 1.53.

<Transparent Substrate>

In order to obtain a transparent laminate having excellent visibility without impairing polarization properties of 3D displays, a transparent substrate having an in-plane retardation value in a certain range is used in the present invention.

In the present invention, an in-plane retardation value of the transparent substrate may be 20 nm or less.

In the present specification, the in-plane retardation value is a value defined by the following formula.

$$\text{In-plane retardation}(Ro) = \Delta N \times d \quad \Delta N = |N_x - N_y|$$

In the formula above, Nx and Ny represent refractive indexes along main axis x, y directions of a refractive index ellipsoid, Nx and Ny represent refractive indexes along the in-plane direction of the substrate, and d represents a thickness (μm; converted into nm as necessary) of the substrate.

The retardation value can be calculated by measuring at a wavelength of 550 nm using a retardation film-optical material inspection device RETS-100 (available from Otsuka Electronics Co., Ltd.).

The retardation value can be adjusted with a material and a thickness of the transparent substrate, and can be appropriately selected to satisfy the predetermined performance.

For example, a substrate of triacetyl cellulose (TAC), polycarbonate (PC), a cycloolefin-based resin (cycloolefin polymer (COP), cycloolefin polymer (COC)), an acrylic resin, a polymethyl pentene resin, an olefin-based resin, etc. can be used. More specifically, a substrate of a TAC film having a film thickness (t) of 117 μm (Ro value: 3 nm), a substrate of a PC film having t of 125 μm (Ro value: 10 nm to 20 nm), a substrate of a PC film having t of 150 μm (Ro value: 15 nm to 20 nm), a substrate of a COP film having t of 100 μm (Ro value: 2 nm), etc. can be used.

An average thickness of the transparent substrate 11 can be appropriately selected depending on the intended use of the transparent laminate 1. For example, the average thickness is preferably 80 μm or greater for use as an eye shield because the transparent substrate that is too thin has insufficient rigidness, which impairs elf-standing of the film during wearing.

In order to obtain a transparent laminate having excellent visibility without impairing polarization properties of 3D displays, although it depends on a retardation value of each base material, it is desirable to set a material or thickness of the substrate to achieve a retardation value of 20 nm or less.

<Structure Layer>

The structure layer contains protrusion portions, depression portions, or both on the surface thereof, and the average distance between the adjacent protrusion portions or the average distance between the adjacent depression portions is equal to or less than a wavelength of visible light.

The structure layer contains a polymerized product of an active energy ray curable resin composition.

The average thickness L (μm) of the structure layer is not particularly limited, and can be appropriately selected depending on the intended purpose.

In the case where an intention is to reduce a weight of a shield or to reduce a material for use, the average thickness is preferably 5 μm or less. In order to prevent interference fringes that occur when a refractive index of a structure layer and a refractive index of a substrate are not matched, a thickness of the structure layer is preferably set to 7 μm or greater to improve appearance characteristics. A thickness of the structure layer is desirably appropriately set depending on the intended purpose. The average thickness L can be calculated by measuring each of the total thickness of the transparent laminate and the thickness of the transparent substrate 10 times by use of a thickness gauge (Litematic VL-50S-B manufactured by Mitutoyo Corporation) to determine the respective average thicknesses, and subtracting the average thickness of the transparent substrate from the average thickness of the transparent laminate.

<<Active Energy Ray Curable Resin Composition>>

The active energy ray curable resin composition includes at least a composition of a (meth)acryloyl group-containing polymerizable compound described below, and may further include a photopolymerization initiator, and other ingredients, such as fillers and various functional additives, according to the necessity.

The composition of a (meth)acryloyl group-containing polymerizable compound includes one or more of (A) below, one or more of (B) below, and one or more of (C) below:

(A) a monofunctional (meth)acryloyl group-containing polymerizable compound;

(B) alkylene glycol di(meth)acrylate; and (C) trifunctional or higher (meth)acrylate.

The (A) monofunctional (meth)acryloyl group-containing polymerizable compound satisfies (A-1) below or (A-2) below:

(A-1) a nitrogen-containing monofunctional (meth)acryloyl group-containing polymerizable compound that includes nitrogen in a structure thereof is included but a nitrogen-free monofunctional (meth)acryloyl group-containing polymerizable compound that does not include nitrogen in a structure thereof is not included, and an amount of the nitrogen-containing monofunctional (meth)acryloyl group-containing polymerizable compound in the active energy ray curable resin composition is 20% by mass or greater; and (A-2) a nitrogen-containing monofunctional (meth)acryloyl group-containing polymerizable compound that includes nitrogen in a structure thereof and a nitrogen-free monofunctional (meth)acryloyl group-containing polymerizable compound that does not include nitrogen in a structure thereof are included, an amount of the nitrogen-containing monofunctional (meth)acryloyl group-containing polymerizable compound in the active energy ray curable resin composition is 20% by mass or greater, and an amount of the nitrogen-free monofunctional (meth)acryloyl group-containing polymerizable compound in the active energy ray curable resin composition is 22% by mass or less.

As described in (A-1) above, in the present invention, a nitrogen-containing monofunctional (meth)acryloyl group-containing polymerizable compound that includes nitrogen in a structure thereof is essentially included as the (A) monofunctional (meth)acryloyl group-containing polymerizable compound. An amount of the nitrogen-containing monofunctional (meth)acryloyl group-containing polymerizable compound in the active energy ray curable resin composition is 20% by mass or greater.

The nitrogen-containing monofunctional (meth)acryloyl group-containing polymerizable compound is necessary because the nitrogen-containing monofunctional (meth)acryloyl group-containing polymerizable compound can exhibit an anchor effect where the nitrogen-containing monofunctional (meth)acryloyl group-containing polymerizable compound partially dissolves a resin component of the transparent substrate and reacts with another resin composition to achieve adhesion to a transparent substrate of a structure layer. When the amount of the nitrogen-containing monofunctional (meth)acryloyl group-containing polymerizable compound is 20% by mass or greater, moreover, sufficient adhesion can be secured even in a heating environment and in a high humidity environment. When the amount is less than 20% by mass, sufficient adhesion to a transparent substrate cannot be obtained and it is also difficult to release the structure layer from a master.

Examples of the nitrogen-containing monofunctional (meth)acryloyl group-containing polymerizable compound include acryloyl morpholine, methyl acryloyl morpholine, diethyl acryl amide, isopropyl acryl amide, hydroxyethyl acryl amide, N-acryloyloxyethylhexahydrophthalimide, and pentamethylpiperidylmethacrylate.

The nitrogen-containing monofunctional (meth)acryloyl group-containing polymerizable compound is preferably a nitrogen-containing monofunctional (meth)acryloyl group-containing polymerizable compound having a cyclic structure including nitrogen in a molecule. The nitrogen-containing monofunctional (meth)acryloyl group-containing polymerizable compound is particularly more preferably acryloyl morpholine.

In the present invention, moreover, as described with (A-2) above, a nitrogen-free monofunctional (meth)acryloyl group-containing polymerizable compound that does not include nitrogen in a structure thereof may be included as the (A) monofunctional (meth)acryloyl group-containing polymerizable compound in addition to the nitrogen-containing monofunctional (meth)acryloyl group-containing polymerizable compound that includes nitrogen in a structure thereof. In this case, as described earlier, an amount of the nitrogen-containing monofunctional (meth)acryloyl group-containing polymerizable compound in the active energy ray curable resin composition is 20% by mass or greater, and an amount of the nitrogen-free monofunctional (meth)acryloyl group-containing polymerizable compound in the active energy ray curable resin composition is 22% by mass or less.

In order to secure flexibility and releasability of the structure layer, it is also effective to include the nitrogen-free (meth)acryloyl group-containing polymerizable compound in an amount of 22% by mass or less. When the nitrogen-free (meth)acryloyl group-containing polymerizable compound is included in an amount of greater than 22% by mass, however, adhesion of the structure layer to the transparent substrate is affected. Therefore, the nitrogen-free (meth)acryloyl group-containing polymerizable compound may be included in an amount of 22% by mass or less.

Examples of the nitrogen-free monofunctional (meth)acryloyl group-containing polymerizable compound include tetrahydrofurfuryl acrylate, methyltetrahydrofurfuryl acrylate, 3,4-epoxycyclohexylmethylmethacrylate, glycidyl methacrylate, 3-ethyl-3-methacryloxymethyloxetane, isobutyl (meth) acrylate, stearyl (meth) acrylate, lauryl (meth) acrylate, isooctyl (meth) acrylate, and isobornylbet-Wacrylate.

The nitrogen-free monofunctional (meth)acryloyl group-containing polymerizable compound is preferably a nitrogen-free monofunctional (meth)acryloyl group-containing polymerizable compound that includes an oxygen-containing cyclic structure per molecule, and particularly the nitrogen-free monofunctional (meth)acryloyl group-containing polymerizable compound is more preferably tetrahydrofuryl acrylate.

The (B) alkylene glycol di(meth)acrylate is (meth)acrylic acid ester of difunctional alkyl alcohol, specifically, difunctional (meth)acrylate of alkyl alcohol as a raw material. Examples of the (B) alkylene glycol di(meth)acrylate include ethylene glycol diacrylate, 1,4-butanediol diacrylate, 1,6-hexanediol diacrylate, 1,9-nonanediol diacrylate, and 1,10-decanediol diacrylate. For example, polyethylene glycol diacrylate, which includes a polyoxyalkylene chain, not an alkyl chain, in a structure, is not included in the (B) alkylene glycol di(meth)acrylate. As exhibited with the results of Comparative Example 4 described later, the transparent laminate including difunctional (meth)acrylate that includes a polyoxyalkylene chain in a structure has a low water contact angle and poor wiping capability of dirt. Accordingly, in the present invention, it is important that difunctional (meth)acrylate does not include oxygen in a structure site other than the structure sites of both ends of (meth)acrylate.

Examples of the (C) trifunctional or higher (meth)acrylate include pentaerythritol triacrylate, trimethylolpropane triacrylate, pentaerythritol tetraacrylate, and ditrimethylolpropane triacrylate.

Among them, it is more preferred that trifunctional (meth)acrylate be included.

In the present invention, more preferred is an embodiment where trifunctional (meth)acrylate is included as the (C) trifunctional or higher (meth)acrylate, or trifunctional (meth)acrylate and trifunctional or higher urethane acrylate are included as the (C) trifunctional or higher (meth)acrylate.

The nitrogen-containing monofunctional (meth)acryloyl group-containing polymerizable compound used as (A) above is a compound having a monofunctional reaction site, and therefore the nitrogen-containing monofunctional (meth)acryloyl group-containing polymerizable compound can be more efficiently reacted by using compounds having polyfunctional reaction sites used as (B) or (C) above.

Moreover, the structure layer tends to be hard when a compound having a polyfunctional reaction site is used, and a protrusion and depression structure tends to be broken when the structure layer is released from the master. Therefore, (meth)acrylic acid ester of alkyl alcohol, which has excellent reactivity owing to a difunctional reaction site and can also impart flexibility, is included as the (B). The hardness of the structure layer can be adjusted with the (B) alkylene glycol di(meth)acrylate.

In the composition of a (meth)acryloyl group-containing polymerizable compound, an amount of the (B) alkylene glycol di(meth)acrylate in the active energy ray curable resin composition is preferably from 5% by mass to 60% by mass.

Moreover, an amount of the (C) trifunctional or higher (meth)acrylate in the active energy ray curable resin composition is preferably from 5% by mass to 24% by mass.

Furthermore, in the case where a few types of (meth)acrylates are included as the (C) trifunctional or higher (meth)acrylate, for example, the case where trifunctional (meth)acrylate and trifunctional or higher urethane acrylate are included, in the active energy ray curable resin composition, the trifunctional (meth)acrylate is preferably included in an amount of from 5% by mass to 24% by mass, and the trifunctional or higher urethane acrylate is preferably included in an amount of from 5% by mass to 24% by mass.

—Photopolymerization Initiator—

Examples of the photopolymerization initiator include a photoradical polymerization initiator, a photo-acid generator, a bisazide compound, hexamethoxymethylmelamine and tetramethoxyglycoluril.

The photoradical polymerization initiator is not particularly limited and can be appropriately selected depending on the intended purpose. Examples of the photoradical polymerization initiator include (2,4,6-trimethylbenzoyl)-diphenyl-phosphine oxide, ethoxyphenyl (2,4,6-trimethylbenzoyl)phosphine oxide, bis(2,6-dimethylbenzoyl)-2,4,4-trimethylpentylphosphine oxide, bis(2,4,6-trimethylbenzoyl)-2,4,4-trimethylpentylphosphine oxide, bis(2,6-dichlorobenzoy)-2,4,4-trimethylpentylphosphine oxide, 1-phenyl 2-hydroxy-2-methylpropan-1-one, 1-hydroxycyclohexyl phenyl ketone, 1-(4-isopropylphenyl)-2-hydroxy-2-methylpropan-1-one, 1,2-diphenylethanedione and methyl phenylglyoxylate.

An amount of the photopolymerization initiator in the active energy ray curable resin composition is not particularly limited and can be appropriately selected depending on the intended purpose. The amount of the photopolymerization initiator is preferably 0.1% by mass to 10% by mass, and more preferably 0.5% by mass to 8% by mass.

—Other Ingredients—

In the present invention, various functional additives, such as fillers below, can be added as long as the additives do not adversely affect the object of the present invention. In the present invention, however, preferred is an embodiment where a lubricant disclosed in PTL 3, which may affect adhesion as described earlier, is not included.

—Fillers—

The fillers are not particularly limited and can be appropriately selected depending on the intended purpose. For example, both inorganic particles and organic particles can be used as the fillers. Examples of the inorganic particles include metal oxide particles of $SiO_2$, $TiO_2$, $ZrO_2$, $SnO_2$, $Al_2O_3$, etc.

The active energy ray curable resin composition is cured by irradiation of active energy rays. The active energy rays are not particularly limited and can be appropriately selected depending on the intended purpose. Examples of the active energy rays include electron beams, ultraviolet light, infrared light, laser light beams, visible light beams, ionizing radiations (X-rays, $\alpha$-rays, $\beta$-rays, $\gamma$-rays and the like), microwaves, and high-frequency waves.

<<Protrusion Portions and Depression Portions>>

As illustrated in FIG. 1A and FIG. 2, a plurality of structures 12a are two-dimensionally arranged on the surface of the structure layer 12 formed on the transparent substrate 11. The structures 12a are preferably periodically two-dimensionally arranged at a short interval (average arrangement pitch) equal to or less than the wavelength band of light for the purpose of a reduction in reflection or an enhancement in permeation.

In the present invention, the interval (pitch) refers to the distance between adjacent protrusion portions, or the distance between adjacent depression portions.

Examples of specific shapes of the structures 12a include cone, column, needle, hemisphere, semioval and polygonal shapes, but are not limited to these shapes, and other shape may be adopted. Examples of the cone shape include a cone shape whose top portion is acuate, a cone shape whose top portion is flat, and a cone shape having a protrusion or depression curved surface on the top portion, but are not limited to these shapes. Examples of the cone shape having a protrusion or depression curved surface on the top portion include a two-dimensionally curved surface shape such as a paraboloid shape. A conical surface may be curved so as to have a depression or protrusion. When a roll master is produced using a roll master exposure apparatus (see FIG. 4) described later, an elliptical cone shape having a protrusion curved surface on the top portion, or an elliptical frustum shape whose top portion is flat may be adopted as the shape of each structure 12a. The shapes such as elliptical, spherical and ellipsoidal shapes here encompass not only shapes such as complete elliptical, spherical and ellipsoidal shapes mathematically defined, but also shapes such as elliptical, spherical and ellipsoidal shapes to which more or less distortion is provided. The flat shape is not limited to an elliptical shape and the like, and may be a round shape.

A cone shape where the slope of the top portion is gentle and gradually more precipitous from the center portion to the bottom portion is preferable from the viewpoint of an enhancement in optical adjustment function. In addition, a cone shape where the slope of the center portion is more precipitous than those of the bottom portion and the top portion, or a cone shape whose top portion is flat is preferable from the viewpoint of an enhancement in optical adjustment function.

In FIG. 1A, FIG. 1B, and FIG. 2, while the structures 12a have the same size, shape and height, the configuration of the structures 12a is not limited thereto, and structures 12a having two or more sizes, shapes and heights may be formed on the substrate surface.

The average aspect ratio (the average height of the protrusion portions/the average distance between the adjacent protrusion portions) of the protrusion portions or the average aspect ratio (the average depth of the depression portions/the average distance between the adjacent depression portions) of the depression portions, of the structures 12a provided on the surface of the structure layer 12, is not particularly limited, can be appropriately selected for any purpose, and is preferably 0.66 to 1.96, more preferably 0.76 to 1.96. When the average aspect ratio is 0.66 or more, low-reflection properties can be enhanced. On the other hand, when the average aspect ratio is 1.96 or less, releasability and the like can be enhanced.

The average arrangement pitch P (referred to as the average distance between adjacent protrusion portions, or the average distance between adjacent depression portions) of the structures 12a is preferably equal to or less than the wavelength band of light for the purpose of an optical adjustment function. The wavelength band of light for the purpose of an optical adjustment function, in the present invention, refers to, for example, the band equal to or less than the wavelength band of visible light (wavelength band from 360 nm to 830 nm).

The average height H of the protrusion portions or the average depth H of the depression portions of the structures 12a is not particularly limited, can be appropriately selected far any purpose, and is preferably 100 nm to 300 nm, more preferably 180 nm to 300 nm, further preferably 180 nm to 230 nm. When the average height H of the protrusion portions or the average depth H of the depression portions of the structures 12a, is 100 nm or more, low-reflection properties can be enhanced. On the other hand, when the average height H of the protrusion portions or the average depth H of the depression portions of the structures 12a is 300 nm or less, releasability and the like can be enhanced.

The average arrangement pitch (average distance (Pm)) of the protrusion portions or depression portions, and the average height of the protrusion portions or the average depth (Hm) of the depression portions can be measured as follows.

[Measurement of Pm (nm) and Hm (nm)]

First, the surface S of the structure layer having protrusion portions or depression portions is observed by an atomic force microscope (AFM), and the pitch between protrusion portions or depression portions, and the height of each protrusion portion or the depth of each depression portion are determined from the cross-section profile of AFM. Such operations are repeatedly conducted at 10 points randomly selected on the surface of the structure layer, and pitches P(1), P(2), . . . , P(10) and heights or depths H(1), H(2), . . . , H(10) are determined.

The pitch between protrusion portions means the distance between the vertices of the protrusion portions. The pitch between depression portions means the distance between the deepest parts of the depression portions. The height of each protrusion portion refers to the height of each protrusion portion with the minimum point of a trough between protrusion portions being defined as a standard. The depth of each depression portion refers to the depth of each depression portion with the maximum point of a peak between depression portions being define as a standard.

Next, such pitches P(1), P(2), . . . , P(10) and heights or depths H(1), H(2), . . . , H(10) are simply averaged out (arithmetically averaged out) to provide the average distance (Pm) between protrusion portions or depression portions and the average height of the protrusion portions or the average depth (Hm) of the depression portions, respectively.

In the AFM observation, in order that the vertex of protrusion or the bottom side of depression of the cross-section profile is consistent with the vertex of a protrusion portion or the deepest part of a depression portion of a stereoscopic shape, the cross-section profile is obtained by cutting out so as to allow the cross-section to pass through the vertex of protrusion portions of a stereoscopic shape to be measured or the deepest part of a depression portion of a stereoscopic shape.

The transparent substrate 11 has an average thickness appropriately selected depending on the application of the transparent laminate 1 and preferably has flexibility and rigidity depending on the application, and may be, for example, formed so as to have an average thickness within the above range.

In addition, while the structure layer 12 is formed with having a proper average thickness depending on the application or whether the structure layer 12 is formed on one surface or both surfaces of the transparent substrate, the structure layer 12 may be, for example, formed within the above range. When the structure layer 12 is formed on the both surfaces, the average thicknesses of the structure layers on the both surfaces are not necessarily the same.

<<Properties of Structure Layer>>

A ratio ($E'_{150}/E'_{50}$) of storage elastic modulus $E'_{150}$ of the structure layer at 150° C. to storage elastic modulus $E'_{50}$ of the structure layer at 50° C. is 0.5 or less.

The ratio is specified based on the insight that a structure layer is excessively hard and therefore releasability from a master is reduced, when a retaining rate of the storage elastic modulus of 50° C. and 150° C. is greater than 0.5 relative to a temperature increase of the master from 50° C. to about 130° C. during production of a transparent laminate. A transparent laminate whose releasability is surely improved can be obtained by specifying $E'_{150}/E'_{50}$ relative to the active energy ray curable resin composition specified in the present invention.

A water contact angle on a surface of the structure layer is preferably 26° or greater, and more preferably 26° or greater but 80° or less.

As described in Examples later, an ink can be wiped out and excellent wiping can be achieved when the water contact angle is 26° or greater.

When the water contact angle is 80° or less, moreover, a shield can be prevented from being fogged when the shield is worn.

<Other Members>

The above-mentioned other members include an intermediate layer, a protection layer, a pressure-sensitive adhesion layer, and an adhesion layer.

<<Intermediate Layer>>

An intermediate layer may also be provided between the transparent substrate and the structure layer depending on various purpose.

The refractive index of the intermediate layer is preferably close to the refractive index of the structure layer in order to prevent the variation in interference. Alternatively, the refractive index of the intermediate layer is preferably between the refractive index of the structure layer and the refractive index of the transparent substrate.

<<Protection Layer>>

The protection layer is not particularly limited and can be appropriately selected depending on the intended purpose, as long as the protection layer is a layer that prevents the structure layer from being damaged in production or molding processing of the transparent laminate in which the structure layer is formed. The protection layer is peeled when the transparent laminate is used.

<<Pressure-Sensitive Adhesion Layer and Adhesion Layer>>

The pressure-sensitive adhesion layer and the adhesion layer are not particularly limited and can be appropriately selected depending on the intended purpose, as long as the pressure-sensitive adhesion layer and the adhesion layer are formed on the transparent substrate and are layers that adhere the transparent laminate to an object to be processed, an adherend and the like.

Figure 10:
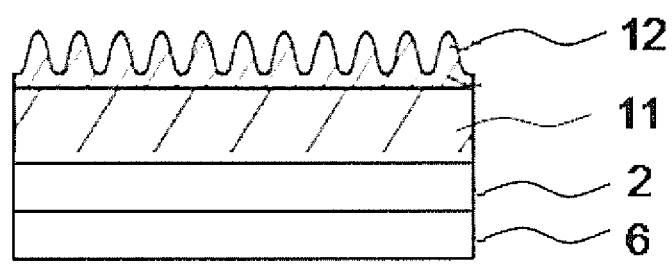
FIG. 10 is a cross-sectional view illustrating one example of a variant of a transparent laminate of the present invention.

As illustrated in FIG. 10, for example, the transparent laminate 1 may have a structure where a pressure-sensitive adhesion layer 2 is disposed at the side of the transparent substrate 11 of the transparent laminate 1, and a light-transmitting base 6 is further disposed.

The transparent laminate is particularly suitable for a film for in-mold molding, a film for insert molding, and a film for overlay molding.

A production method of the transparent laminate is not particularly limited and can be appropriately selected depending on the intended purpose. Examples of the production method include a production method described below.

<Production Method of Transparent Laminate>

Examples of a production method of the transparent laminate include a production method including an uncured resin layer formation step, and a structure layer formation step. The production method may further include other step according to the necessity.

<<Uncured Resin Layer Formation Step>>

The uncured resin layer formation step is not particularly limited and can be appropriately selected depending on the intended purpose, as long as the uncured resin layer formation step is a step including applying an active energy ray curable resin composition onto a transparent substrate to form an uncured resin layer.

The transparent substrate is as described in the descriptions of the transparent laminate.

The active energy ray curable resin composition is as described in the descriptions of the structure layer of the transparent laminate.

The uncured resin layer is formed by applying the active energy ray curable resin composition onto the transparent substrate, and optionally drying the applied active energy ray curable resin composition. The uncured resin layer may be a solid film, or a film having a fluidity owing to a low molecular weight curable component included in the active energy ray curable resin composition.

The coating method is not particularly limited and can be appropriately selected for any purpose, and examples thereof include wire bar coating, blade coating, spin coating, reverse roll coating, die coating, spray coating, roll coating, gravure coating, microgravure coating, lip coating, air knife coating, curtain coating and comma coating methods, and a dipping method.

The uncured resin layer is not cured because of being not irradiated with an active energy ray.

In the uncured resin layer formation step, the intermediate layer of the transparent substrate where the intermediate layer is formed may also be coated with the active energy ray curable resin composition to form the uncured resin layer.

The intermediate layer is as described in the section of the transparent laminate.

<<Structure Layer Formation Step>>

The structure layer formation step is not particularly limited as long as it is a step of closely attaching the uncured resin layer to a transfer master having any of fine s protrusion and depression portions, and irradiating the uncured resin layer to which the transfer master is closely attached, with an active energy ray, to cure the uncured resin layer, thereby transferring any of the fine protrusion portions and depression portions to form a structure layer, and can be appropriately selected depending on the intended purpose.

—Transfer Master—

The transfer master has any of fine protrusion and depression portions.

The material, the size and the structure of the transfer master are not particularly limited, and can be appropriately selected depending on the intended purpose.

The method for forming any of fine protrusion and depression portions of the transfer master is not particularly limited and can be appropriately selected depending on the intended purpose, and such any of fine protrusion and depression portions is preferably formed by etching the surface of the transfer master with a photoresist having a predetermined pattern shape, as a protection film.

—Active Energy Ray—

The active energy ray is not particularly limited as long as it is an active energy ray that cures the uncured resin layer, can be appropriately selected depending on the intended purpose, and is, for example, as described in the section of the transparent laminate.

A specific example of the structure layer formation step is here described with reference to the drawings.

A transfer master where any of fine protrusion and depression portions is formed by etching the surface of the transfer master with a photoresist having a predetermined pattern shape, as a protection film, is used to form a structure layer.

[Configuration of Transfer Master]

Figure 3A:
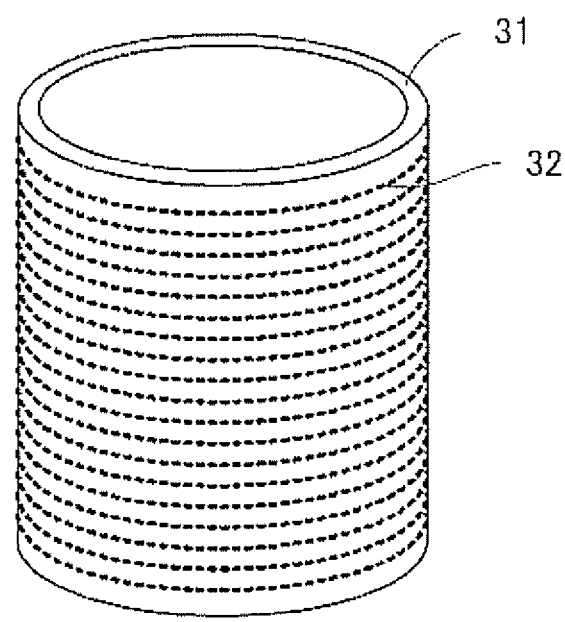
FIG. 3A is a perspective view illustrating one configuration example of a roll master being a transfer master.
Figure 3B:
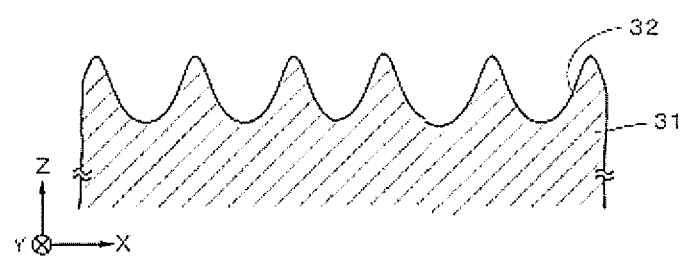
FIG. 3B is a plan view representing a part of the roll master illustrated in FIG. 3A, in an enlarged manner.

FIG. 3A is a perspective view illustrating one configuration example of a roll master being a transfer master. FIG. 3B is a cross-sectional view representing a part of the roll master illustrated in FIG. 3A, in an enlarged manner. A roll master 31 is a transfer master for production of a transparent laminate having the above configuration, more specifically, a master for molding of a plurality of protrusion portions or depression portions on the surface of the structure layer. The roll master 31 has, for example, a columnar or cylindrical shape, and the columnar surface or cylindrical surface serves as a molded surface for molding of a plurality of protrusion portions or depression portions on the surface of the structure layer. For example, a plurality of structures 32 are two-dimensionally arranged on the molded surface. In FIG. 3B, the structures 32 have a depression shape on the molded surface. As the material of the roll master 31, for example, glass can be used, but the material is not limited thereto.

The plurality of structures 32 arranged on the molded surface of the roll master 31 and the plurality of protrusion portions or depression portions arranged on the surface of the structure layer are in a reverse depression and protrusion relationship. That is, the arrangement, the size, the shape, the arrangement pitch, the height or depth, the aspect ratio and the like of the structures 32 of the roll master 31 are the same as those of the protrusion portions or depression portions of the structure layer.

[Roll Master Exposure Apparatus]

Figure 4:
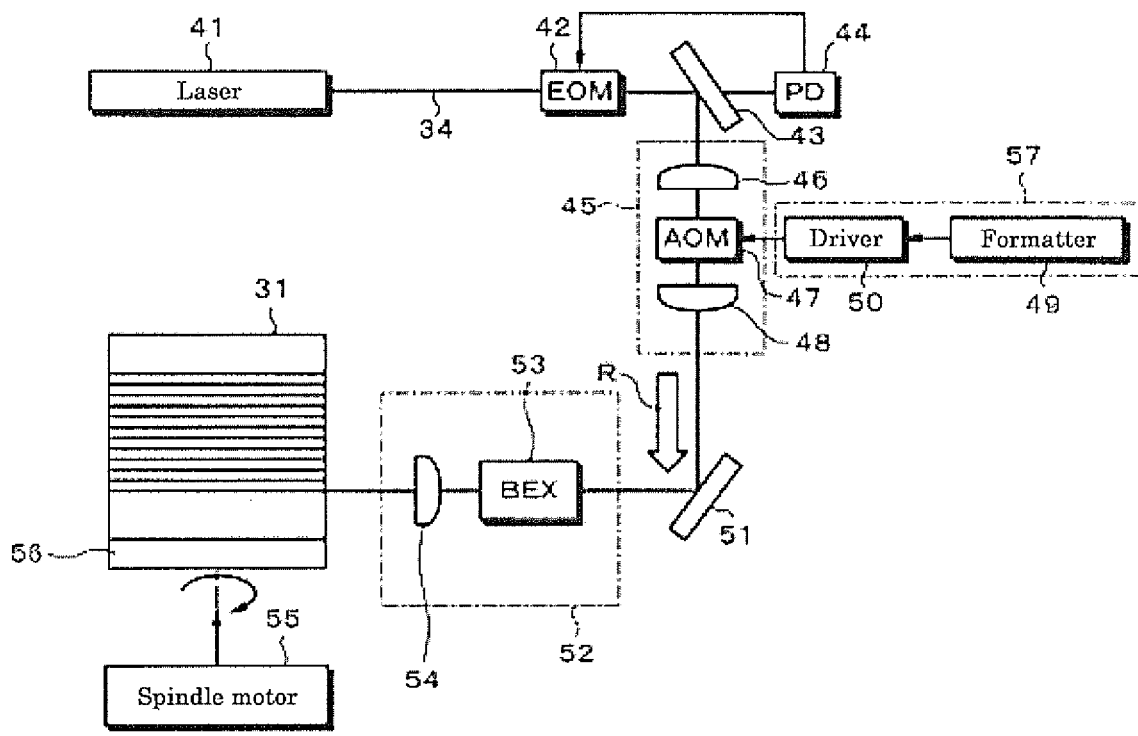
FIG. 4 is a schematic view illustrating one configuration example of a roll master exposure apparatus which produces a roll master.

FIG. 4 is a schematic view illustrating one configuration example of a roll master exposure apparatus for producing a roll master. The roll master exposure apparatus is configured based on an optical disk recording apparatus.

A laser light source 41 is a light source that exposes a resist attached in the form of a film onto the surface of the roll master 31 as a recording medium, and is, for example, one that emits laser light 34 for recoding at a wavelength λ, of 266 nm. The laser light 34 emitted from the laser light source 41 goes straight as parallel beam, and enters an electro-optical element (EOM: Electro Optical Modulator) 42. The laser light 34 penetrating through the electro-optical element 42 is reflected in a mirror 43, and guided to a modulation optical system 45.

The mirror 43 is configured from a polarization beam splitter, and has a function of reflecting one polarization component and allowing other polarization component to penetrate through the mirror. The polarization component penetrating through the mirror 43 is received in a photo diode 44, and the electro-optical element 42 is controlled based on such a light reception signal for phase modulation of the laser light 34.

In the modulation optical system 45, the laser light 34 is collected by a collective lens 46 to an acousto-optic modulator (AOM) 47 made of glass ($SiO_2$) and the like. The laser light 34 is diffused due to intensity modulation by the acousto-optic modulator 47, and thereafter formed into parallel beam by a lens 48. The laser light 34 emitted from the modulation optical system 45 is reflected by a mirror 51, and horizontally and parallel guided onto a moving optical table 52.

The moving optical table 52 includes a beam expander 53 and an objective lens 54. The laser light 34 guided to the moving optical table 52 is formed into a desired beam shape by the beam expander 53, and thereafter a resist layer located on the roll master 31 is irradiated with such laser light 34 via the objective lens 54. The roll master 31 is mounted on a turntable 56 connected to a spindle motor 55. While the roll master 31 is then rotated and also the laser light 34 is moved in the height direction of the roll master 31, a resist layer formed on the peripheral side surface of the roll master 31 is intermittently irradiated with the laser light 34, thereby allowing a resist layer exposure step to be performed. A latent image formed has a substantially elliptical shape having a longitudinal axis in the circumferential direction. Movement of the laser light 34 is performed by movement of the moving optical table 52 in the direction of arrow R.

An exposure apparatus includes a control mechanism 57 that allows a latent image corresponding to a two-dimensional pattern to be formed into a resist layer. The control mechanism 57 includes a formatter 49 and a driver 50. The formatter 49 includes a polarity inversion portion, and the polarity inversion portion controls the timing of irradiation of the resist layer with the laser light 34. The driver 50 receives the output from the polarity inversion portion and controls the acousto-optic modulator 47.

[Resist Film Formation Step]

Figure 5A:
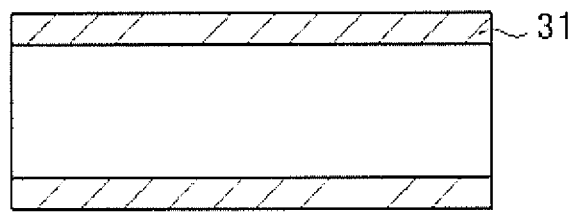
FIG. 5A is a process drawing for describing one example of a process for producing a roll master.
Figure 5B:
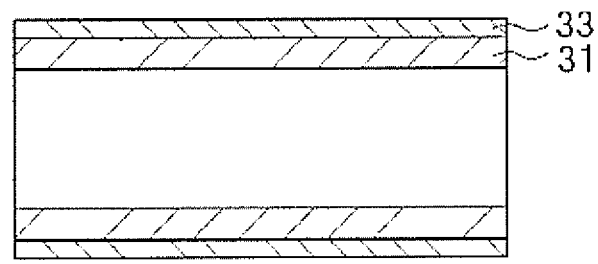
FIG. 5B is a process drawing for describing one example of a process for producing a roll master.

First, a columnar or cylindrical roll master 31 is prepared as illustrated in the cross-sectional view of FIG. 5A. The roll master 31 is, for example, a glass master. Next, a resist layer (for example, photoresist) 33 is formed on the surface of the roll master 31 as illustrated in the cross-sectional view of FIG. 5B. Examples of the material of the resist layer 33 include an organic resist and an inorganic resist. Examples of the organic resist include a novolac type resist and a chemically amplified type resist. Examples of the inorganic resist include a metal compound.

[Exposure Step]

Figure 5C:
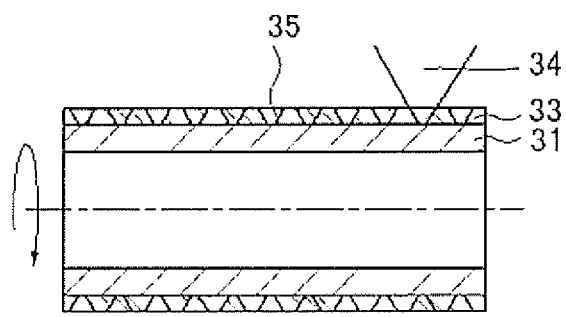
FIG. 5C is a process drawing for describing one example of a process for producing a roll master.

Next, as illustrated in the cross-sectional view of FIG. 5C, the resist layer 33 formed on the surface of the roll master 31 is irradiated with laser light (exposing beam) 34. Specifically, the roll master 31 is mounted on the turntable 56 of the roll master exposure apparatus illustrated in FIG. 4, and the roll master 31 is rotated and also the resist layer 33 is irradiated with the laser light (exposing beam) 34. Here, while the laser light 34 is moved in the height direction of the roll master 31 (direction parallel with the center axis of the columnar or cylindrical roll master 31), the resist layer 33 is intermittently irradiated with the laser light 34 and the entire surface thereof is thus exposed. Thus, a latent image 35 according to the trajectory of the laser light 34 is formed on the entire surface of the resist layer 33 at, for example, a pitch comparable with a wavelength of visible light.

The latent image 35 is, for example, arranged so as to form a plurality of rows of tracks on the surface of the roll master, and also forms a lattice pattern. The latent image 35 has, for example, an elliptical shape whose longitudinal direction corresponds to the track extending direction.

[Development Step]

Figure 5D:
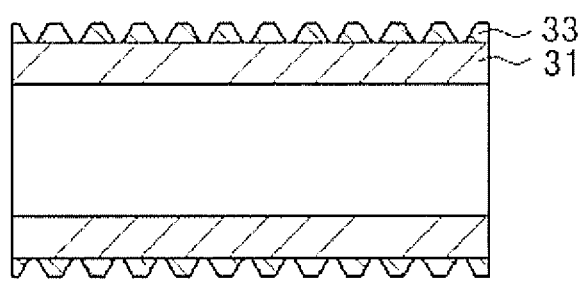
FIG. 5D is a process drawing for describing one example of a process for producing a roll master.

Next, for example, while the roll master 31 is rotated, a developer is dropped onto the resist layer 33 and the resist layer 33 is subjected to a development treatment. Thus, as illustrated in the cross-sectional view of FIG. 5D, a plurality of openings are formed in the resist layer 33. When the resist layer 33 is formed by a positive type resist, an area exposed to the laser light 34 is increased in terms of the dissolution speed in the developer as compared with an area not exposed, and therefore, a pattern corresponding to a latent image (exposed area) 35 is formed on the resist layer 33 as illustrated in the cross-sectional view of FIG. 5D. The pattern of openings is a predetermined lattice pattern such as a hexagonal lattice pattern or a quasi-hexagonal lattice pattern.

[Etching Step]

Figure 5E:
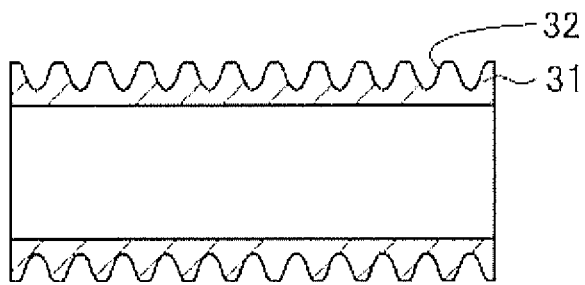
FIG. 5E is a process drawing for describing one example of a process for producing a roll master.

Next, the pattern (resist pattern) of the resist layer 33 formed on the roll master 31 is used as a mask to subject the surface of the roll master 31 to an etching treatment. Thus, a structure (depression portion) 32 having a cone shape can be obtained as illustrated in the cross-sectional view of FIG. 5E. The cone shape is preferably, for example, an elliptical cone shape or an elliptical frustum shape whose longitudinal direction corresponds to the track T extending direction. As the etching, for example, dry etching or wet etching can be used. An etching treatment and an ashing treatment can be here alternately performed to thereby form a pattern of cone-shaped structures 32. As described above, an intended roll master 31 is obtained.

[Transfer Treatment]

Figure 6A:
FIG. 6A is a process drawing for describing one example of a process for transferring fine protrusion portions or depression portions by a roll master.

A transparent substrate 11 where an uncured resin layer 36 is formed as illustrated in the cross-sectional view of FIG. 6A is prepared.

Figure 6B:
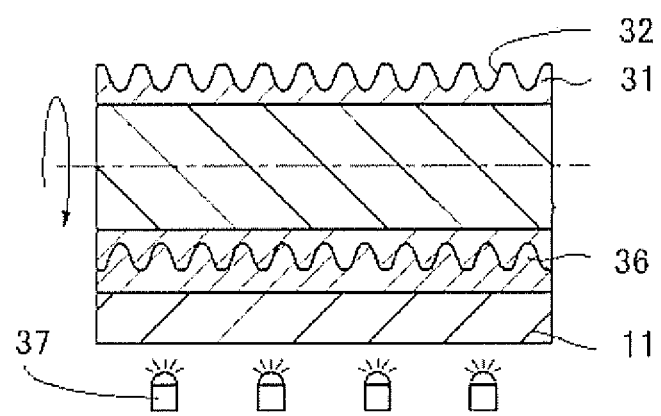
FIG. 6B is a process drawing for describing one example of a process for transferring fine protrusion portions or depression portions by a roll master.
Figure 6C:
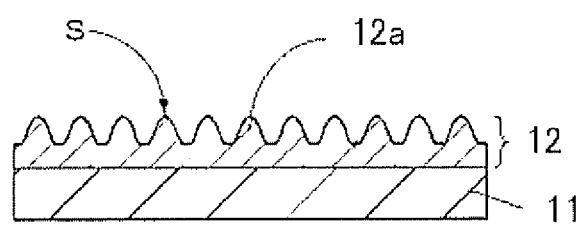
FIG. 6C is a process drawing for describing one example of a process for transferring fine protrusion portions or depression portions by a roll master.

Next, as illustrated in the cross-sectional view of FIG. 6B, the roll master 31 and the uncured resin layer 36 formed on the transparent substrate 11 are closely attached, and the uncured resin layer 36 is irradiated with an active energy ray 37 to cure the uncured resin layer 36, transferring any of fine protrusion and depression portions. A structure layer 12 where any of fine protrusion and depression portions 12a is formed and the transparent substrate 11 integrated therewith are peeled to thereby provide the transparent laminate 1 of the present invention (FIG. 6C).

When the transparent laminate is one including the structure layer on both surfaces of the transparent substrate as illustrated in FIG. 1B, it is obtained through the further following step.

Figure 7A:
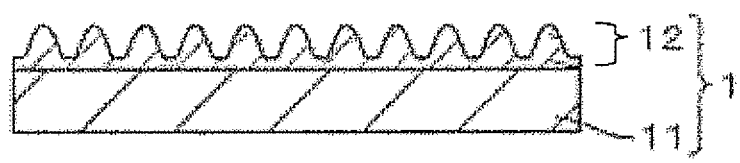
FIG. 7A is a process drawing for describing another example of a process for transferring fine protrusion portions or depression portions by a roll master.
Figure 7B:
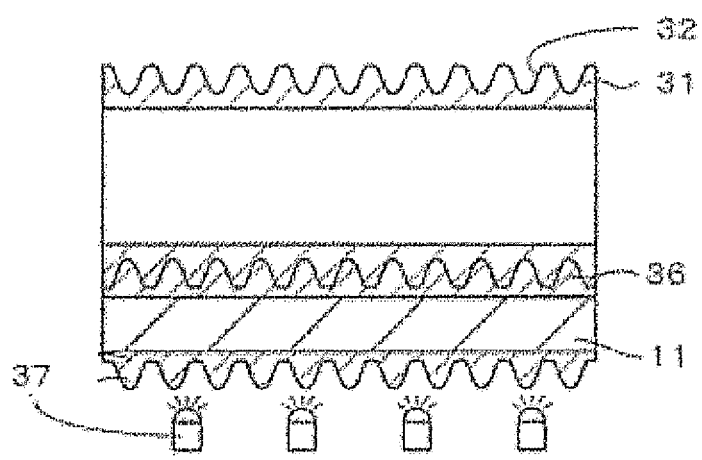
FIG. 7B is a process drawing for describing another example of a process for transferring fine protrusion portions or depression portions by a roll master.
Figure 7C:
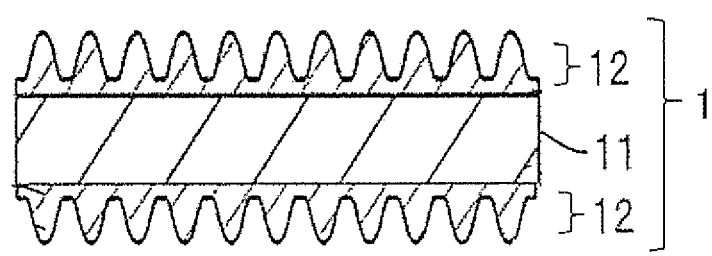
FIG. 7C is a process drawing for describing another example of a process for transferring fine protrusion portions or depression portions by a roll master.

The transparent laminate 1 obtained as above, where the structure layer is formed on one surface, is used (FIG. 7A), furthermore the roll master 31, and the uncured resin layer 36, with which an opposite surface of the transparent substrate 11 where the structure layer is formed on one surface is coated, are closely attached, thereafter the uncured resin layer 36 is cured by irradiation of the uncured resin layer 36 with an energy ray from an energy ray source 37, such as ultraviolet light, and the transparent substrate 11 integrated with the structure layer 12 cured is peeled, as illustrated in FIG. 7B. Thus, as illustrated in FIG. 7C, a transparent laminate 1 which includes the structure layer 12 having a plurality of structures 12a, on both surfaces of the transparent substrate 11, is obtained.

<Applied Example of Transparent Laminate of Present Invention>

Figure 8A:
FIG. 8A is a plan view of an eye shield of one embodiment of the present invention.
Figure 8B:
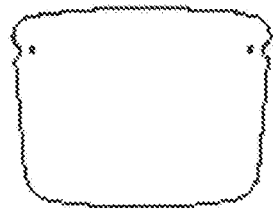
FIG. 8B is a plan view of a face shield of one embodiment of the present invention.

The transparent laminate of the present invention exhibits excellent results on all of items, such as anti-reflection properties, transparency, visibility, anti-fogging, wiping capability, adhesion, and releasability with a desired balance. Using these advantages, the transparent laminate can be applied for an eye shield illustrated in FIG. 8A or a face shield illustrated in FIG. 8B, as a face protection mask. Moreover, the transparent laminate can be applied for a display film, a display surface film (particularly suitably used as a film used an inner side because of excellent anti-fogging) used for a display surface of a switch board, a distribution board, etc., a display surface film (particularly suitably used as a film used an inner side because of excellent anti-fogging) used for a display surface of a display device of a motor bicycle, and the like. Moreover, the transparent laminate can be applied for a shield of a helmet used for sports of bicycles (bicycles and motor bicycles)) or four-wheel vehicles, or sports goggles used for horseracing.

Among them, the transparent laminate is preferably used as a face protection shield for medical use, or an optical element for face, such as a face shield corresponding to a 3D display function.

(Optical Element for Face)

Utilizing advantages of the transparent laminate of the present invention, such as anti-reflection properties, transparency, visibility, anti-fogging, wiping capability, adhesion, and releasability, the transparent laminate can be preferably used as an optical element for face.

For example, a face protection mask for medical use using the optical element for face of the present invention excels in anti-fogging, and has excellent transparency.

The face protection mask can be obtained by detachably mounting the optical element for face of the present invention on a fixture of an optical element in a shape of goggles or a face mask, or fixing the optical element for face of the present invention in a face mask.

Figure 9A:
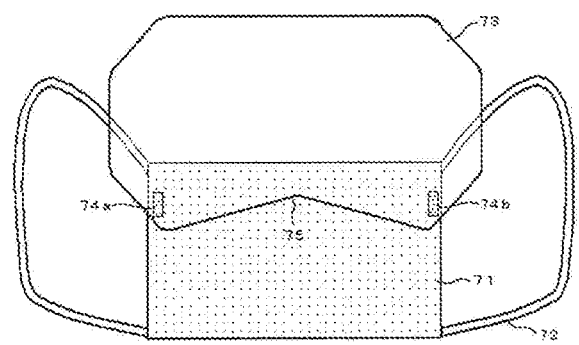
FIG. 9A is a plan view of a face protection mask of one embodiment of the present invention.
Figure 9B:
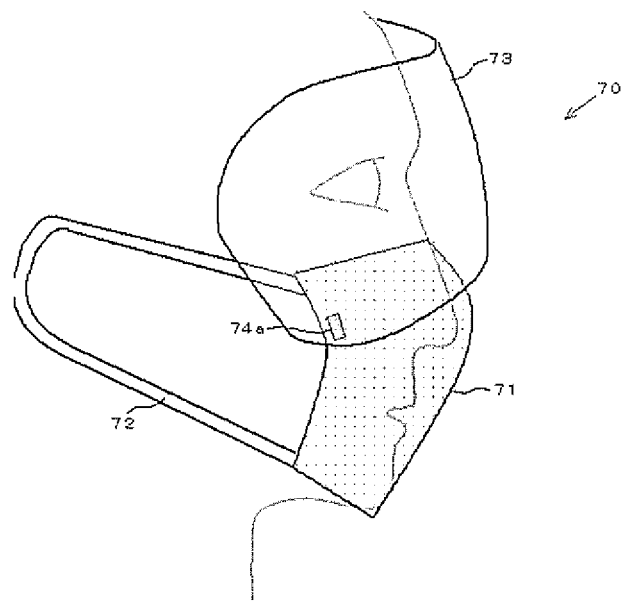
FIG. 9B is a perspective view of the face protection mask of one embodiment of the present invention, worn on the face.

FIG. 9A is a plan view of one embodiment of a face protector 70 in which the optical element for face 1 of the present invention is fixed on a face mask 71 as an eye shield 73, and FIG. 9B is a perspective view of the face protector 70 worn on the face.

The face mask 71 covers a nose, mouth, and part of chin of a user, and is held on a face with a string 72, etc.

On the other hand, the optical element 1 for face protection is fixed as an eye shield 73 to the face mask 71 in junction regions 74a and 74b, the eye shield preventing any liquid or flying object from coming into the eyes of the wearer without obstructing the visual field of the wearer.

The face protection optical element 1 used as the eye shield above is used by obtaining a transparent laminate according to the above-described production method, followed by cutting into a predetermined size. Note that, a surface protection film may be disposed on a surface of the transparent laminate in order to product the surface of the transparent laminate during production and processing of an object, such as a face protector, including the cutting step.

An article including the transparent laminate of the present invention can be formed by in-mold molding, insert molding or overlay molding.

EXAMPLES

Hereinafter, the present invention is more specifically described with reference to Examples and Comparative Examples, but the present invention is not limited thereto.

In Examples below, respective measurements and evaluations were performed as follows.

<Optical Properties>

Total light transmittance (Tt (%)) and a haze value (haze (%)) were measured by a haze meter available from a haze meter available from MURAKAMI COLOR RESEARCH LABORATORY according to JIS K 7361.

<Water Contact Angle (°)>

Between 11 seconds and 20 seconds after dripping 1 µL of water, a contact angle was measured every second by an automatic contact angle measuring device CA-V available from Kyowa Interface Science Co., Ltd., and an average value of the measured values was taken as a contact angle. Note that, the contact angle was an average value of two values, a value for a machine direction (MD) and a value for a traverse direction (TD).

<Adhesion>

A peeling test was performed according to JIS K 5400 by cutting a sample into 100 squares using a cut guide (tool) available from COTEC, and using a predetermined cellophane tape. The number of remained adhered squares was measured, and adhesion was evaluated by determining a result as 100 when all of the squares were still adhered and as 0 when all of the squares were peeled.

<Wiping Capability>

A commercial aqueous ink available from TSUKINEKO Co., Ltd. was diluted to a 100-fold dilution, and the dilution was dripped by 1 drop using a pipette. Thereafter, the ink dilution was wiped out with cotton non-woven fabric.

A case where the dirt was wiped out was evaluated as I that meant excellent, and a case where the dirt was remained (color was remained) was evaluated as II that meant that it was unable to wipe out.

<Storage Elastic Modulus>

The active energy ray curable resin composition was applied to give a film thickness of about 100 µm, while nipping between release-treated PET films each having a thickness of 50 µm. Thereafter, UV irradiation was performed to cure the active energy ray curable resin composition to produce a clear film.

The clear film was punched out using a punching die having a width of 6 mm and a length of 40 mm, and a storage elastic modulus (GPa) of the resultant at temperature from room temperature to 200° C. was measured by means of RSA3 available from TA Instruments under the conditions that an applied frequency was 10 Hz, a heating rate was 10° C./min, and a sample measuring distance was 10 mm.

A ratio ($E'_{150}/E'_{50}$) of the storage elastic modulus $E'_{150}$ to the storage elastic modulus $E'50$ was obtained from the measurement results of the storage elastic modulus $E'_{150}$ at 150° C. and the storage elastic modulus $E'_{50}$ at 50° C.

<Anti-Fogging>

Anti-fogging was when a mask formed of the transparent laminate of the present invention was worn and fitted as a shield for a face. As a result, a case where fogging did not occur was evaluated as I that meant that visibility was excellent, and a case where fogging occurred was evaluated as II.

<Releasability>

In the following production step, a state where a structure layer was released from a master roll was observed and releasability was evaluated based on the following criteria.

A case where release from the master roll was performed without any problem was evaluated as I, and a case where a problem occurred in releasing, such as part of the structure layer was remained on the master roll, or the structure layer was whitened, or the structure layer could not be released was evaluated as II. Note that, the whitening means that a cohesive failure of a coating film (structure layer) is partially caused to form a whitened area when the transparent laminate is released, because the adhesion to the master is strong. Once the coating film is remained on the master, a surface disturbance of the structure layer occurs and whitening tends to occur when transfer is additionally performed.

Example 1

<Production of Transfer Master (Glass Roll Master) Having Fine Depression Portions>

First, a glass roll master having an outer diameter of 126 mm was prepared, and a resist layer was formed on the surface of the glass roll master as follows. That is, a photoresist was diluted with a thinner to a mass ratio of 1/10, and the columnar surface of the glass roll master was coated with the resist diluted, by a dipping method, so that the average thickness was about 70 nm, thereby forming a resist layer. Next, the glass roll master was conveyed to the roll master exposure apparatus illustrated in FIG. 4, and the resist layer was exposed to thereby allow a latent image being continuous in a helix and forming a hexagonal lattice pattern among three adjacent rows of tracks to be patterned on the resist layer. Specifically, a region where a hexagonal lattice exposure pattern was to be formed was irradiated with laser light at 0.50 mJ/m in an image shape, to form a hexagonal lattice exposure pattern.

Next, the resist layer on the glass roll master was subjected to a development treatment, and the resist layer on the area exposed was dissolved for development. Specifically, the glass roll master not subjected to development was mounted on the turntable of a developing machine not illustrated, and a developer was dropped on the surface of the glass roll master with the glass roll master being rotated together with the turntable, to develop the resist layer on the surface. Thus, a resist glass master where the resist layer was opened in the hexagonal lattice pattern was obtained.

Next, a roll etching apparatus was used to perform plasma etching in a $CHF_3$ gas atmosphere. Thus, etching was advanced in only an area of the hexagonal lattice pattern, exposed from the resist layer, on the surface of the glass roll master and no etching was advanced in other area due to the resist layer serving as a mask, to form depression portions having an elliptical cone shape on the glass roll master. Here, the amount (depth) of etching was adjusted by the etching time. Finally, the resist layer was completely removed by $O_2$ ashing, thereby providing a glass roll master having a depression-shaped hexagonal lattice pattern.

<Production of Transparent Laminate>

Next, the roll master obtained as above was used to produce a transparent laminate by UV imprinting. Specifically, such production was performed as follows.

| -Preparation of ultraviolet ray (UV) curable resin composition for structure layer- | |
|---|---|
| Acryloyl morpholine (ACMO) (available from KJ Chemicals Corporation) | 29.7% by mass |
| Tetrahydrofurfuryl acrylate (THFA) (Biscoat V#150, available from OSAKA ORGANIC CHEMICAL INDUSTRY LTD.) | 14.3% by mass |
| 1,6-Hexanediol diacrylate (HDDA) (available from Miwo) | 14.3% by mass |
| Pentaerythritol triacrylate (A-TMM-3, available from SHIN-NAKAMURA CHEMICAL CO., LTD.) | 22.5% by mass |

| -continued |  |
|---|---|
| -Preparation of ultraviolet ray (UV) curable resin composition for structure layer- | |
| Urethane acrylate (UV-1700B, available from The Nippon Synthetic Chemical Industry Co., Ltd.) | 16.2% by mass |
| 2-Hydroxy-1-{4-[4-(2-hydroxy-2-methyl-propionyl)-benzyl]-phenyl}-2-methyl-propan-1-one (polymerization initiator: Irg 127 (available from BASF S. E)) | 3.0% by mass |

Note that, the Miwon above means Miwon Specialty Chemical Co., Ltd.

A composition liquid composed of substances other than the polymerization initiator among the UV curable resin composition above was mixed for 2 hours at 50° C., followed by adding the polymerization initiator. The resultant was further mixed for 30 minutes at 50° C., and was left to stand for 10 hours or longer to naturally degassing the air bubbles of the mixed liquid.

As a transparent substrate, a triacetyl cellulose (TAC) film (thickness (t) 117 μm) was prepared.

On the transparent substrate, the UV curable resin composition obtained in the above-described manner was applied to give a thickness of about 4 μm. Subsequently, the applied UV curable resin composition was nipped with the glass roll master obtained in the above-described manner, and ultraviolet rays was applied from the side of the transparent substrate at 500 mJ/cm$^2$ to cure the resin. Thereafter, the resultant was released from the master to thereby obtain a transparent laminate.

Next, on a surface of the transparent laminate opposite to the surface where the protrusion and depression shapes were formed, a structure layer having a protrusion and depression structure was formed in the same manner as above, to thereby obtain the transparent laminate to which the structure layers were provided at the both sides of the transparent substrate.

An average thickness of the structure layer of the obtained transparent laminate was 3 μm, an average distance (Pm) of the protrusion portion was 178 nm, an average height (Hm) of the protrusion portion was 245 nm, and an average aspect ratio (Hm/Pm) was 1.38.

The obtained transparent laminate was measured and evaluated on each item of the total light transmittance (Tt), haze value, water contact angle (°), adhesion, wiping capability, storage elastic modulus, anti-fogging, and releasability according to the above-described methods. The results are presented in Table 2-1.

Examples 2 to 6

Each transparent laminate was obtained in the same manner as in Example 1 except that the ultraviolet curable resin composition for the structure layer in Example 1 was changed to each composition shown in Table 1-1 below.

In order to evaluate properties of each transparent laminate obtained, the same measurements and evaluations as in Example 1 were performed. The results are shown in Table 2-1.

Note that, in Table 1 (Tables 1-1 to 1-3 may be collectively referred to as Table 1), as trimethylolpropane triacrylate (TMPTA), Miramer M300 (available from Miwon) was used, and as polyethylene glycol diacrylate (the repeating number of the ethylene glycol chain=9), A-400 (available from SHIN-NAKAMURA CHEMICAL CO., LTD.) was used.

Comparative Examples 1 to 12

Each transparent laminate was obtained in the same manner as in Example 1 except that the ultraviolet curable resin composition for the structure layer in Example 1 was changed to each composition shown in Table 1-2 and Table 1-3 below.

In order to evaluate properties of each transparent laminate obtained, the same measurements and evaluations as in Example 1 were performed. The results were shown in Table 2-2 and Table 2-3. Note that, in Comparative Example 6, a sample of the transparent laminate could not be produced because the structure layer was too hard, and therefore a storage elastic modulus could not be measured. Among Comparative Examples, moreover, there were some cases where the results of releasability and adhesion were extremely bad and the properties required for the present invention could not be obtained, therefore the rest of the evaluation items were not measured. In such a case, an evaluation result was presented as '-' in the table.

TABLE 1-1

|  |  | Components | Ex. 1 | Ex. 2 | Ex. 3 | Ex. 4 | Ex. 5 | Ex. 6 |
|---|---|---|---|---|---|---|---|---|
| Mono-functional | (A) | acryloyl morpholine | 29.7 | 22.9 | 21.4 | 31.1 | 44.6 | 20.0 |
|  | (A) | tetrahydrofurfuryl acrylate | 14.3 | 22.0 | 21.1 | — | — | — |
| Bi-functional | (B) | 1,6-hexanediol diacrylate | 14.3 | 22.0 | 26.3 | 25.0 | 29.2 | 53.8 |
|  |  | polyethylene glycol diacrylate | — | — | — | — | — | — |
| Tri-functional | (C) | pentaerythritol triacrylate | 22.5 | 17.4 | 16.3 | 23.2 | — | — |
|  | (C) | trimethylolpropane triacrylate | — | — | — | — | 23.2 | 23.2 |
| Deca-functional | (C) | urethane acrylate | 16.2 | 12.7 | 11.9 | 17.7 | — | — |
| Polymerization initiator |  | Irg 127 | 3.0 | 3.0 | 3.0 | 3.0 | 3.0 | 3.0 |
|  |  | Total | 100 | 100 | 100 | 100 | 100 | 100 |

TABLE 1-2

|  |  | Components | Comp. Ex. 1 | Comp. Ex. 2 | Comp. Ex. 3 | Comp. Ex. 4 | Comp. Ex. 5 | Comp. Ex. 6 |
|---|---|---|---|---|---|---|---|---|
| Mono-functional | (A) | acryloyl morpholine | 37.6 | 24.1 | 19.6 | 29.0 | 25.7 | 9.7 |
|  | (A) | tetrahydrofurfuryl acrylate | — | 23.5 | — | — | 25.0 | — |
| Bi-functional | (B) | 1,6-hexanediol diacrylate | 10.0 | 17.7 | 51.6 | — | 12.6 | 23.2 |
|  |  | polyethylene glycol diacrylate | — | — | — | 30.0 | — | — |
| Tri-functional | (C) | pentaerythritol triacrylate | 28.6 | 18.3 | 14.9 | 22.0 | 19.5 | — |
|  | (C) | trimethylolpropane triacrylate | — | — | — | — | — | 64.1 |
| Deca-functional | (C) | urethane acrylate | 20.8 | 13.4 | 10.9 | 16.0 | 14.2 | — |
| Polymerization initiator |  | Irg 127 | 3.0 | 3.0 | 3.0 | 3.0 | 3.0 | 3.0 |
|  |  | Total | 100 | 100 | 100 | 100 | 100 | 100 |

TABLE 1-3

|  |  | Components | Comp. Ex. 7 | Comp. Ex. 8 | Comp. Ex. 9 | Comp. Ex. 10 | Comp. Ex. 11 | Comp. Ex. 12 |
|---|---|---|---|---|---|---|---|---|
| Mono-functional | (A) | acryloyl morpholine | — | 44.6 | 20.0 | 9.7 | — | — |
|  | (A) | tetrahydrofurfuryl acrylate | 44.6 | 29.1 | 53.8 | 64.0 | 19.4 | 9.7 |
| Bi-functional | (B) | 1,6-hexanediol diacrylate | 29.1 | — | — | — | 54.3 | 64.0 |
|  |  | polyethylene glycol diacrylate | — | — | — | — | — | — |

TABLE 1-3-continued

|  | | Components | Comp. Ex. 7 | Comp. Ex. 8 | Comp. Ex. 9 | Comp. Ex. 10 | Comp. Ex. 11 | Comp. Ex. 12 |
|---|---|---|---|---|---|---|---|---|
| Tri-functional | (C) | pentaerythritol triacrylate | — | — | — | — | — | — |
|  | (C) | trimethylolpropane triacrylate | 23.3 | 23.3 | 23.2 | 23.3 | 23.3 | 23.3 |
| Deca-functional | (C) | urethane acrylate | — | — | — | — | — | — |
|  | Polymerization initiator | Irg 127 | 3.0 | 3.0 | 3.0 | 3.0 | 3.0 | 3.0 |
|  | Total |  | 100 | 100 | 100 | 100 | 100 | 100 |

TABLE 2-1

|  | Ex. 1 | Ex. 2 | Ex. 3 | Ex. 4 | Ex. 5 | Ex. 6 |
|---|---|---|---|---|---|---|
| Releasability | I | I | I | I | I | I |
| Adhesion (cross-cut test) | 100 | 100 | 100 | 100 | 100 | 100 |
| Water contact angle (°) | 40 | 55 | 65 | 26 | 62 | 75 |
| Anti-fogging | I | I | I | I | I | I |
| Wiping capability | I | I | I | I | I | I |
| $E'_{50}$ (GPa) | 1.73 | 1.17 | 1.2 | 0.97 | 1.99 | 1.95 |
| $E'_{150}$ (GPa) | 0.8 | 0.24 | 0.28 | 0.48 | 0.49 | 0.95 |
| $E'_{150}/E'_{50}$ | 0.46 | 0.21 | 0.23 | 0.49 | 0.25 | 0.49 |
| Total light transmittance (%) | 98.7 | 98.8 | 98.9 | 98.8 | 98.8 | 98.7 |
| Haze value (%) | 0.4 | 0.4 | 0.4 | 0.4 | 0.4 | 0.4 |

TABLE 2-2

|  | Comp. Ex. 1 | Comp. Ex. 2 | Comp. Ex. 3 | Comp. Ex. 4 | Comp. Ex. 5 | Comp. Ex. 6 |
|---|---|---|---|---|---|---|
| Releasability | II | I | I | I | II | II |
| Adhesion (cross-cut test) | — | 40 | 0 | 100 | 0 | 0 |
| Water contact angle (°) | — | 52 | 70 | 16 | — | 92 |
| Anti-fogging | — | I | I | I | I | II |
| Wiping capability | — | I | I | II | — | — |
| $E'_{50}$ (GPa) | 1.85 | 1.91 | 1.79 | 1.67 | — | Could not be produced as it was too hard, and could not be measured |
| $E'_{150}$ (GPa) | 1.15 | 0.51 | 0.69 | 0.68 | — |  |
| $E'_{150}/E'_{50}$ | 0.62 | 0.27 | 0.49 | 0.41 | — |  |
| Total light transmittance (%) | Whitened, not measured | 98.7 | 98.8 | 98.7 | 98.7 | 98.8 |
| Haze value (%) | Whitened, not measured | 0.4 | 0.4 | 0.4 | 0.4 | 0.4 |

TABLE 2-3

|  | Comp. Ex. 7 | Comp. Ex. 8 | Comp. Ex. 9 | Comp. Ex. 10 | Comp. Ex. 11 | Comp. Ex. 12 |
|---|---|---|---|---|---|---|
| Releasability | II | II | II | II | II | II |
| Adhesion (cross-cut test) | 0 | 0 | 0 | 0 | 0 | 0 |
| Water contact angle (°) | 90 | 60 | 78 | 83 | — | — |
| Anti-fogging | II | I | I | II | — | — |
| Wiping capability | I | I | I | I | — | — |
| $E'_{50}$ (GPa) | 1.15 | 1.86 | 1.47 | — | — | — |
| $E'_{150}$ (GPa) | 0.17 | 0.04 | 0.04 | — | — | — |
| $E'_{150}/E'_{50}$ | 0.09 | 0.02 | 0.02 | — | — | — |
| Total light transmittance (%) | 98.7 | 98.7 | 98.8 | 98.7 | 98.8 | 98.8 |
| Haze value (%) | 0.4 | 0.4 | 0.4 | 0.4 | 0.4 | 0.4 |

It was confirmed from the experiment results above that the transparent laminate of the present invention was a transparent laminate having excellent anti-fogging, wiping capability, adhesion to a substrate, and releasability from a master.

REFERENCE SINGS LIST 1 transparent laminate
2 pressure-sensitive adhesion layer
6 light-transmitting base
11 transparent substrate
12 structure layer
12a structure
31 roll master
32 structure
33 resist layer
34 laser light
35 latent image
36 uncured resin layer 37 active energy ray
41 laser light source
42 electro-optical element
43 mirror
44 photo diode
45 modulation optical system
46 collective lens
47 acousto-optic modulator
48 lens
49 formatter
50 driver
51 mirror
52 moving optical table
53 beam expander
54 objective lens
55 spindle motor
56 turntable
57 control mechanism
70 face protection tool
71 face mask
72 string
73 eye shield
74a, 74b junction regions
75 depression

The invention claimed is:

1. A transparent laminate comprising:
a transparent substrate; and
a structure layer,
wherein the structure layer contains protrusion portions, depression portions, or both on a surface of the structure layer, and an average distance between the adjacent protrusion portions or an average distance between the adjacent depression portions is equal to or less than a wavelength of visible light,
the structure layer includes a polymerized product of an active energy ray curable resin composition,
the active energy ray curable resin composition includes a composition of a (meth)acryloyl group-containing polymerizable compound, the composition of a (meth)acryloyl group-containing polymerizable compound includes one or more of (A) below, one or more of (B) below, and one or more of (C) below:
(A) a monofunctional (meth)acryloyl group-containing polymerizable compound;
(B) alkylene glycol di(meth)acrylate; and
(C) trifunctional or higher (meth)acrylate;
the (A) monofunctional (meth)acryloyl group-containing polymerizable compound satisfies (A-1) below or (A-2) below:
(A-1) a nitrogen-containing monofunctional (meth)acryloyl group-containing polymerizable compound that includes nitrogen in a structure thereof is included but a nitrogen-free monofunctional (meth)acryloyl group-containing polymerizable compound that does not include nitrogen in a structure thereof is not included, and an amount of the nitrogen-containing monofunctional (meth)acryloyl group-containing polymerizable compound in the active energy ray curable resin composition is 20% by mass or greater; and
(A-2) a nitrogen-containing monofunctional (meth)acryloyl group-containing polymerizable compound that includes nitrogen in a structure thereof and a nitrogen-free monofunctional (meth)acryloyl group-containing polymerizable compound that does not include nitrogen in a structure thereof are included, an amount of the nitrogen-containing monofunctional (meth)acryloyl group-containing polymerizable compound in the active energy ray curable resin composition is 20% by mass or greater, and an amount of the nitrogen-free monofunctional (meth)acryloyl group-containing polymerizable compound in the active energy ray curable resin composition is 22% by mass or less,
the (C) trifunctional or higher (meth)acrylate consists of trifunctional (meth)acrylate, wherein an amount of the trifunctional (meth)acrylate in the active energy ray curable resin composition is from 5% by mass to 24% by mass, and
a ratio ($E'_{150}/E'_{50}$) of storage elastic modulus $E'_{150}$ of the structure layer at 150° C. to storage elastic modulus $E'_{50}$ of the structure layer at 50° C. is 0.5 or less.

2. The transparent laminate according to claim 1, wherein the nitrogen-containing monofunctional (meth)acryloyl group-containing polymerizable compound includes a cyclic structure containing nitrogen in a molecule thereof.

3. The transparent laminate according to claim 2, wherein the nitrogen-containing monofunctional (meth)acryloyl group-containing polymerizable compound is acryloyl morpholine.

4. The transparent laminate according to claim 1, wherein the nitrogen-free monofunctional (meth)acryloyl group-containing polymerizable compound includes a cyclic structure containing oxygen in a molecule thereof.

5. The transparent laminate according to claim 4, wherein the nitrogen-free monofunctional (meth)acryloyl group-containing polymerizable compound is tetrahydrofurfuryl acrylate.

6. The transparent laminate according to claim 1, wherein a water contact angle on a surface of the structure layer is 26° or greater.

7. The transparent laminate according to claim 1, wherein an in-plane retardation value of the transparent substrate is 20 nm or less.

8. An optical element for face comprising:
the transparent laminate according to claim 1.

* * * * *